United States Patent [19]
Van Brussel et al.

[11] Patent Number: 5,997,840
[45] Date of Patent: Dec. 7, 1999

[54] CHIRAL SOLID CATALYST, ITS PREPARATION AND ITS USE FOR THE PRODUCTION OF SUBSTANTIALLY ENANTIOMERICALLY PURE PRODUCTS

[75] Inventors: Willy Van Brussel, Wetteren; Michel Renard, Brussels; Diedrik Tas, Ninove; Rudy Parton, Winksele; Pierre A. Jacobs, Gooik, all of Belgium; Vilas Hare Rane, Maharashtra State, India

[73] Assignee: K.V. Leuven Research & Development, Leuven, Belgium

[21] Appl. No.: 09/051,557

[22] PCT Filed: Oct. 10, 1996

[86] PCT No.: PCT/BE96/00108

§ 371 Date: Jul. 13, 1998

§ 102(e) Date: Jul. 13, 1998

[87] PCT Pub. No.: WO97/14500

PCT Pub. Date: Apr. 24, 1997

[30] Foreign Application Priority Data

Oct. 13, 1995 [EP] European Pat. Off. ............ 95202760

[51] Int. Cl.[6] ............... C01B 11/00; C01C 11/00; C01D 11/00; C22B 11/00
[52] U.S. Cl. ............... 423/659; 502/62; 502/74; 560/1; 568/700; 585/16
[58] Field of Search ............... 502/62, 74, 208, 502/213; 423/659; 560/1; 568/700; 585/16

[56] References Cited

U.S. PATENT DOCUMENTS 4,554,262  11/1985  Dessau .
5,736,480  4/1998  Davis et al. ............... 502/155
5,817,877  10/1998  Hartwig et al. ............... 564/399
5,821,389  10/1998  Briggs et al. ............... 568/454
5,827,794  10/1998  Davis et al. ............... 502/162

FOREIGN PATENT DOCUMENTS 366 390 A2   5/1990   European Pat. Off. .
0 419 334 A1 3/1991   European Pat. Off. .
419334 A1    12/1994  European Pat. Off. .
0 633 238 A2 1/1995   European Pat. Off. .
WO 93/04775  3/1993   WIPO .

OTHER PUBLICATIONS

Mikami et al., "Asymmetric Catalysis of Diels–Alder Cycloadditions by an MS–Free Binaphthol–Titanium Complex: Dramatic Effect of MS, Linear vs Positive Nonlinear Relationship, and Synthetic Applications", J. Am. Chem. Soc. 116, pp. 2812–2820, 1994.

*Primary Examiner*—Thomas Dunn
*Attorney, Agent, or Firm*—Knobbe, Martens, Olson & Bear, LLP

[57] ABSTRACT

The invention relates to a chiral solid catalyst containing a BEA topology zeolite and a metal-binap complex and to a process for the production of substantially enantiomerically pure products from prochiral starting material with the catalyst. The BEA topology zeolite may be a BETA zeolite, an acid BEA topology zeolite, an acid NU-2 zeolite, or an ammonium BEA topology zeolite. The metal in the metal-binap complex is ruthenium, iridium, nickel, or rhodium. The zeolite is normally impregnated with a solution of the metal-binap complex. The method is applicable to asymmetric hydrogenation of beta functionalized ketones, betaketoesters, functionalized olefins, and α, β-unsaturated functionalized olefins.

25 Claims, No Drawings

CHIRAL SOLID CATALYST, ITS PREPARATION AND ITS USE FOR THE PRODUCTION OF SUBSTANTIALLY ENANTIOMERICALLY PURE PRODUCTS

The present application is the U.S. national phase under 35 U.S.C. §371 of International Application No. PCT/BE96/00108, filed Oct. 10, 1996.

During the last decade, the utilisation of pure enantiomers in biology has increased exponentially, implying their economic importance. The search for methods to obtain pure enantiomers is given top priority by pharmaceutical and related companies.

Asymmetric hydrogenation is one of the most promising methods to obtain enantiomerically pure products. It has been widely investigated during the past decade. In general, two types of asymmetric hydrogenation catalysts can be distinguished: heterogeneous catalysts, based on metal (Ni, Pt)—loaded carriers (silica, alumina, . . . ) modified with chiral molecules and homogeneous transition-metals complexes. The second group of catalysts has superior properties as far as activity and enantioselectivity are concerned. The heterogeneous catalysts however are favourable from a technical and industrial point of view as they allow continuous operation and easy recovery and regenerability of the expensive catalysts.

Therefore, it is of utmost relevance to be able to develop chiral heterogeneous catalysts which possess the properties of transition metal complexes as far as activity and selectivity are concerned with both the technical and economic advantages of the heterogeneous systems.

Some attempts to synthesise this type of catalysts have been described in literature. A. Corma, M. Iglesias, C. del Pino, F. Sanchez, *J.Chem.Soc.Chem.Commun.*, (1991). 1253–1255 developed an asymmetric hydrogenation catalysts based on a rhodium-complex, anchored on USY-zeolite via covalent bounding. The system suffers from the need for a relatively high temperature (65° C.) and has only been described for the hydrogenation of dehydroamino-acid derivatives.

The immobilisation of di-rhodium complexes via covalent bounding on silica has been investigated for the hydrogenation of dehydroamino acid derivatives (A. Kinting, H. Krause, M. Capka, *J.Mol.Catal.*, 33 (1985). 215–223, M. Eisen, J. Blum, H. Schumann, B. Gorella, *J.Mol.Catal.* 56 (1989). 329–337). Leaching of the catalytic complexes from the solid catalyst into the liquid phase could not be avoided. Moreover, the enantioselectivities obtained, are rather low. The hydrogenation of functionalised ketones has been carried out with a similar catalyst (J. F.Carpentier, F. Agbossou, A. Mortreux, *Tertrahedron: Asymmetry.* 6(1) (1995). 39–42). Low activity and enantioselectivity however are the important constraints of the system.

Another approach towards complex immobilisation is the use of ion exchangers with cationic or anionic complexes. R. Selke, K. Haupke, W. H. Krause, *J.Mol.Catal.*, 56 (1989). 315–328 performed the hydrogenation of dehydroamino acid derivatives with high selectivity using a cationic rhodium complex, exchanged on a sulphonated resin. The system, however, lacks mechanical stability and is limited with respect to solvent choice.

The most versatile complexes in the field of asymmetric hydrogenations are the binap (2,2'bis(diphenylphosphino)-1,1'-binaphthyl))-based complexes (R. Noyori, *Chem.Soc.Rev.*, 187 (1989)). Until now, only one successful attempt has been made to immobilise this type of complexes. K. T. Wan, M. E. Davis, *J.Catal.*, 148 (1994). 1–8, K. T. Wan, M. E. Davis, *Nature*, 370 (1994). 449–450, K. T. Wan, M. E. Davis, *J.Catal.*, 152 (1995), 25–30 developed a water-soluble analogue of binap by direct sulphonation. The ruthenium complex of this ligand is immobilised by the supported-aqueous-phase method. This technology basically uses two immiscible liquid phases (an aqueous phase and an organic phase). The catalyst is dissolved in the aqueous phase, whereas substrate and products are dissolved in the organic phase. To increase the contact area between both phases, the aqueous phase is adsorbed on a solid with a high specific surface area (third phase). The heterogenised complex catalyses the hydrogenation of 2-(6'-methoxy-2'-naphthyl) acrylic acid to naproxen, an anti-inflammatory agent. One of the main disadvantages of the system, however, is that sulphonation of the complex is required, which is difficult and time-consuming to perform. Moreover, the system is triphasic and the number of substrates that react is limited.

Another very important reaction in the field of asymmetric synthesis is the hydrogenation of β-ketoesters. However, all reports concerning this reaction use homogeneous catalysts and require temperatures higher than 80° C. and hydrogen pressures of at least 80 atm. S. A. King, A. S. Thompson, A. O. King, T. R. Verhoeven, *J.Org.Chem.*, 57 (1992), 6689–6691 discovered that the addition of strong acids like HCl or sulphuric acid enables the reaction to be performed in milder conditions (40° C. and 40 atm. hydrogen pressure).

The enantioselectivity is generally described by the enantiomeric excess (e.e.) of the reaction mixture, defined by the relative excess of one enantiomer to the other (% e.e. of $R=100 \cdot ([R]-[S])/([R]+[S])$, in which $[R]$ and $[S]$ stand for the concentrations of both enantiomers in the reaction mixture).

In an attempt to immobilise binap based complexes via impregnation on zeolites, it was surprisingly found that, when a zeolite, preferably a zeolite of the BEA topology, is impregnated with a metal-binap containing solution, a highly active and enantioselective solid catalyst is generated, catalysing among others the hydrogenation of β-ketoesters at room temperature. Preferably, the BEA topology zeolite is a BETA zeolite. Acid, ammonium and metal BEA topology zeolite are possible. Surprisingly, a combination of surface properties and zeolite topology seems to be determining the catalyst activity and enantioselectivity.

Accordingly, the present invention provides chiral solid catalysts, comprising a zeolite, preferably a BEA topology zeolite provided with a metal-binap complex.

It appears that large particle zeolites have a low catalyst activity. Accordingly, it is preferred to use zeolites especially BEA topology zeolites in the form of particles of smaller size, such as in general a size of 0.005–1.0 μm, preferably 0.01–0.5 μm, more preferably 0.02–0.1 μm.

Zeolites comprising a BEA topology are disclosed in Atlas of Zeolite Structure Types by W. M. Meier & D. H. Olson, $3^{rd}$ revised edition, 1992, Butterworth-Heinemann, p. 58–59. Examples of such BEA topology zeolites are BETA zeolite $Na_n[Al_nSi_{64-n}O_{128}]$ with n<7 (Tschernichite), or NU-2 zeolite having an X-ray defraction pattern comparable to that of BETA zeolite, and disclosed in EP-A-0055046.

Typical synthesis recipes ate described in Synthesis of High-Silica Alumino-silicate Zeolites, Studies in Surface Science and Catalysis, 33, 1987, p. 16. It may as well be synthesised by the fluoride method (P. Caullet, J. L. Guth, A. C. Faust, F. Raatz, J. F. Joly, J. M. Deves, EP-A-0419334).

Furthermore, EP-A-0633238, U.S. Pat. No. 4,554,262, WO-A-9304775 and EP-A-0366390 also describe asymetric catalysts and/or zeolite catalysts.

It is noted that in the zeolite Al is partially or completely substituted by a metal ion, such as Fe. For instance in the alumino-silicate BETA zeolite Al may partially or completely be substituted by Fe (R. Kulmar, A. Thangaraj, R. N. Bath, P. Ratnasamy, Zeolites, 10 (1990) 85), B (S. Zones, D. Holtermann, L. W. Jossens, D. S. Santilly, A. Rainis, J. N. Ziemer, PCT WO91/00777), Ga (M. A. Camblor, J. Perez-Pariente, V. Fornes, Zeolites, 12 (1992) 280) or by Ti (M. A. Camblor, A. Corma, A. Martinez, J. Perez-Pariente, J. C. S. Chem. Commun. (1992) 589).

According to another embodiment one of the ligands of the metal-binap complex is R- or S-binap, see Appl. Catal. A:128 (1995) 171.

Preferably, BEA topology zeolite is the Brönsted acid (H)-form.

Zeolites can be described as crystalline metallosilicates, consisting of a three-dimensional network of $Si_4$ and $MO_4$ tetrahedra, sharing corner oxygen atoms. The most important group of zeolites are the aluminosilicate zeolites, where the metal atom M is aluminium. The substitution of trivalent aluminium for tetravalent silicon results in an excess negative charge, which is compensated by cations. The chemical composition of aluminosilicate zeolites is generally represented by $M_{x/n}(AlO_2)_x(SiO_2)_y(H_2O)_z$, in which n is the valence of the charge compensating cations M, and the ratio x/y is smaller than or equal to unity because $AlO_4$ tetrahedra are sharing corners selectivity with $SiO_4$ tetrahedra according to the Lowenstein rule. The presence of protons as counter ions yields acid sites.

Prior art techniques have resulted in the formation of a great variety of synthetic zeolites. These zeolites have come to be designated by letter or other convenient symbols, as illustrated by zeolite X (U.S. Pat. No. 2,882,244), zeolite Y (U.S. Pat. No. 3,130,007), ZK-5 (U.S. Pat. No. 3,347,195), ZK-4 (U.S. Pat. No. 3,314,752), zeolite beta (U.S. Pat. No. 3,308,069), ZSM-5/ZSM-11 intermediate compositions (U.S. Pat. No. 4,229,424), ZSM-5 (U.S. Pat. No. 3,702,886), ZSM-11 (U.S. Pat. No. 3,709,979), ZSM-12 (U.S. Pat. No. 3,832,449), ZSM-23 (U.S. Pat. No. 4,076,842), ZSM-35 (U.S. Pat. No. 4,016,245), ZSM-38 (U.S. Pat. No. 4,046,859) and ZSM-48 (U.S. Pat. No. 4,375,573), merely to name a few.

Zeolite beta is highly disordered intergrowth of at least two polymorphs A and B. The pore structure of zeolite beta is both polymorph A and B can be described as a three-dimensional network, with straight 12-ring channels parallel to a and b, and with tortuous 12-ring paths along the c-direction. The aperture of the channels measures 0.73*0.68 nm for the straight channels along a and b, and 0.55*0.55 nm along c.

The catalyst of the invention can be used as a powder but can also be spray-dried with silica or alumina gel to obtain 8–120 μm granules. It can be transformed into pellets and extrudates via existing technologies.

In order to be able to dissolve substrate and reaction products, the use of a polar solvent is preferred. Solvent polarity can be described by the dielectric constant e of the solvent (N. S. Isaacs, *Physical organic chemistry*, Longman Scientific and Technical, p. 184 (1987) such as $\epsilon$ is 10–100, preferably 30–80. Possible solvents for the reaction system are therefore water, ethylene glycol, polyethylene glycol, glycerol and other related solvents, all showing $\epsilon$-values exceeding that of methanol.

Many different starting materials can be hydrogenated according to the invention, with high enantioselectivity. Functionalised olefines (itaconic acid, geraniol, geranial) and functionalised ketones (methylacetoacetate, ethylacetoacetate, ethylchloroacetoacetate) can be hydrogenated at a high rate and with high enantioselectivity.

Asymmetric synthesis can be done by this type of catalyst. More typically the catalyst shows a high enantioselective recognition of hydrogen and is particularly useful in the reduction of prochiral unsaturated substrates, including allylic alcohols, α, β-unsaturated carboxylic esters or acids, α-(acylamino)acrylic acids, cyclic enamides, of functionalised ketones, of prochiral ketones with heteroatom functional group at α, β or γ position. The catalyst may be used as well for asymmetric isomerisation of allylic systems such as allylic amines, isoprenic amines, for carbon-carbon bond formation in hydroformylation, hydrocyanation, Heck-type reactions and allylic alkylations.

The catalyst according to the invention can be produced by common procedures using on the one hand the BEA topology zeolite and on the other hand the metal-binap complex. The catalyst may be obtained by contacting these materials, for instance by impregnation. It is to be noted that any other suitable process may be used for the production of the chiral solid catalyst according to the present invention.

Compared to the "classical" catalyst preparation consisting in the impregnation of binap complexes on zeolites (e.g. in methanol), the applicant has devised preparation methods consisting in either the simultaneous or the successive impregnation of zeolites by the constituents of the binap complex, namely the binap ligand and the metal by forming the complex in situ on the zeolite.

EXAMPLE 1

Preparation of the Catalyst According to the Invention (R-enantiomer) Using Zeolite BETA and (R)Ru-Binap 0.3 g of acid BETA zeolite—obtained from PQ corp. with a $SiO_2/Al_2O_3$ molar ratio of 21.6 and an average crystal size of 0.05 μm, determined by scanning electron microscopy is impregnated with 0.0017 g of the R-enantiomer of the binap complex ([2,2'-Bis(diphenylphosphino)-1,1'-binaphthyl] chloro(p-cymene)-ruthenium chloride), dissolved in 0.5 g of methanol. The mixture is dried for 3 hours under nitrogen flow. A dry yellowish powder is obtained.

EXAMPLE 2

Preparation of the Catalyst with Higher Loading According to the Invention 0.5 g of acid BETA zeolite—obtained from PQ corp. with a $SiO_2/Al_2O_3$ molar ratio of 21.6 and an average crystal size of 0.05 μm, determined by scanning electron microscopy— is impregnated with 0.01 g of the R-enantiomer of the binap complex ([2,2'-Bis(diphenylphosphino)-1,1'-bil]chloro(p-cymene)-ruthenium chloride), dissolved in a mixture of 0.5 g of methanol and 0.5 g of chloroform, for 3 hours under nitrogen flow. A dry yellowish powder is obtained that is used for IR characterization of the catalyst.

EXAMPLE 3

Hydrogenation of Methylacetoacetate According to the Invention 0.3 gram of the catalyst, prepared according to example 1, is contacted with a mixture of 1.7 g of methylacetoacetate and 7.5 g of ethylene glycol. The reaction is carried out at room temperature with an initial hydrogen pressure of 63 atm in a 10 ml stirred batch microreactor. After 6 days the reaction has reached 80% methylacetoacetate conversion with an enantiomeric excess (% ee) of more than 95% of R-methylhydroxybutyrate.

EXAMPLE 4
Comparative Hydrogenation of Methylacetoacetate Using Sulphonated Ru-Binap Catalyst The hydrogenation of methylacetoacetate at 80° C. and 60 atm with supported aqueous phase catalyst (0.0026 g of sulphonated Ru-binap (0.1 g of zeolite A+5 g of chloroform/cyclohexane (1:1)+0.8 g of methylacetoacetate) yields a methylacetoacetate conversion of 0.0%.

EXAMPLE 5
Homogeneous Asymmetric Hydrogenation of a Naphthylalanine Precursor Using (R)Ru-Binap Catalyst A solution of 0.5 g ethyl-1-acetamido-2-(2-naphthyl)-acrylate (0.0018 mol) and 0.02 g R-enantiomer of the Binap-Ru complex ((2,2'-Bis(diphenylphosphino)-1,1'-binaphthyl)chloro(p-cymene)-ruthenium chloride) (S/C=100) in 25 ml degased methanol was vigorously stirred under hydrogen (100 psi) for 22 h at room temperature. The solution was analyzed by Chiral HPLC to show 99% conversion and an enantiomeric excess (% ee) of 80.0%. Removal of solvent left a residue that, after stirring in 10 ml of methyl tert.butylether gave a white solid of (D)-ethyl-1-acetamido-2-(2-naphthylalanine)ester (Yield=54%; % ee=89.5%). The calculated Turn Over Frequency is ±0.1 mol/mol.min.

EXAMPLE 6
Heterogeneous Asymmetric Hydrogenation of a Naphthylalanine Precursor According to the Invention A solution of 0.5 g ethyl-1-acetamido-2-(2-naphthyl) acrylate (0.0018 mol) and 2.9 g (R)-Binap-Ru on Zeolite catalyst, prepared as described in example 1 (S/C of 100), in 25 ml degased methanol was vigorously stirred under hydrogen (100 psi) for 3 h at room temperature. Centrifugation of the slurry left a solution which was analyzed by Chiral HPLC to show 100% conversion and an enantiomeric excess (% ee) of 82.3%. Removal of solvent left a colourless residue that, after crystallisation in toluene gave a white solid of (D)-ethyl-1-acetamido-2-(2-naphthylalanine)ester (Yield=85%; % ee=98.8%). The calculated Turn Over Frequency is ±1 mol/mol.min.

EXAMPLE 7
Heterogeneous Asymmetric Hydrogenation of a Naphthylalanine Precursor According to the Invention and Recycle of the Catalyst 0.5 g Ethyl-1-acetamido-2-(2-naphthyl)-acrylate (0.0018 mol) was added to a 25 ml degased methanol suspension of recovered (R)-Binap-Ru on Zeolite catalyst of example 6. The resulting suspension was vigorously stirred under hydrogen (100 psi) for 48 h at room temperature. Centrifugation of the slurry left a solution which was analyzed by Chiral HPLC to show 90% conversion and an enantiomeric excess (% ee) of 82.1%. Removal of solvent left a colourless residue that, after stirring in 10 ml of methyl tert.butylether gave a white solid of (D)-ethyl-1-acetamido-2-(2-naphthylalanine)ester.

EXAMPLE 8
Heterogeneous Asymmetric Hydrogenation of a Naphthylalanine Precursor According to the Invention and Reuse of the Filtrate 0.5 g Ethyl-1-acetamido-2-(2-naphthyl)-acrylate (0.0018 mol) was added to the filtrate left after recovery of the (R)-Binap-Ru on Zeolite catalyst of example 6. The resulting solution was vigorously stirred under hydrogen (100 psi) for 48 h at room temperature. Analysis by Chiral HPLC shows 0% conversion of the added substrate.

EXAMPLE 9
Heteroaeneous Asymmetric Hydrogenation of a Naphthylalanine Precursor According to the Invention Using a Small Amount of Catalyst.

A solution of 0.5 g ethyl-1-acetamido-2-(2-naphthyl)-acrylate (0.0018 mol) and 0.58 g (R)-Binap-Ru on Zeolite catalyst, prepared as described in example 1 (S/C of 500), in 25 ml degased methanol was vigorously stirred under hydrogen (100 psi) for 72 h at room temperature. Centrifugation of the slurry left a solution which was analyzed by Chiral HPLC to show 98% conversion and an enantiomeric excess (% ee) of 78.5%. Removal of solvent left a colourless residue that, after crystallisation in toluene gave a white solid of (D)-ethyl-1-acetamido-2-(2-naphthylalanine)ester (Yield=85%; % ee=91.4%).

EXAMPLE 10
Heterogeneous Asymmetric Hydrogenation of a Naphthylalanine Precursor According to the Invention with Successive Substrate Addition To a hydrogenation mixture, obtained as described in example 6, was added 0.5 g ethyl-1-acetamido-2-(2-naphthyl)-acrylate (0.0018 mol) and the slurry was vigorously stirred under nitrogen (100 psi) for 24 hours at room temperature. This process was repeated four times. Centrifugation of the slurry left a solution which was analyzed by Chiral HPLC to show 72% conversion and an enantiomeric excess (% ee) of 78.4% in (D)-ethyl-1-acetamido-2-(2-naphthylalanine)ester.

EXAMPLE 11
Heterogeneous Asymmetric Hydroaenation of Itaconic Acid According to the Invention 0.3 g of the catalyst, prepared according to example 1, is contacted with a mixture of itaconic acid in 10 ml of methanol. The reaction is carried out at room temperature with constant hydrogen pressure of 1 atm in a stirred batch microreactor. After 2 days the reaction has reached 100% conversion with an enantiomeric excess (% ee) of 80% of S-methylsuccinic acid.

EXAMPLE 12
Homogeneous Asymmetric Hydrogenation of Itaconic Acid

A homogeneous mixture of 0.0017 g of R-Ru-Binap complex and 0.02 g of itaconic acid in 10 ml of methanol was hydrogenated using the reaction conditions according to example 11; a 100% conversion was obtained after 2 days with an % ee of 51%.

EXAMPLE 13
Preparation of the Catalyst According to the Invention (S-enantiomer) Using Zeolite BETA and (S)Ru-Binap 0.3 g of acid BETA zeolite—obtained from PQ corp. with a $SiO_2/Al_2O_3$ molar ratio of 21.6 and an average crystal size of 0.05 $\mu$m, determined by scanning electron microscopy—is impregnated with 0.0017 g of the S-enantiomer of the Binap complex ([2,2'-Bis(diphenylphosphino)-1,1'-binaphthyl]chloro(p-cymene)-ruthenium chloride), dissolved in 0.5 g of methanol and dried for 3 hours under nitrogen flow. A dry yellowish powder is obtained.

EXAMPLE 14
Hydrogenation of Geraniol According to the Invention 0.3 gram of the catalyst, prepared according to example 13, is contacted with a mixture of 1.7 g of geraniol and 7.5 g of ethylene glycol. The reaction conditions are according to example 3. After 6 days the reaction has reached 80% conversion with an enantiomeric excess (% ee) of more than 99% of R-citronellol.

EXAMPLE 15
Hydrogenation of Methylacetoacetate According to the Invention

The catalyst used is prepared according to the example 13 and the reaction conditions are as described in example 3 but, instead of ethylene glycol, polyethyleneglycol is used as solvent. After 6 days, the conversion is 11% with more than 96% ee of S-methylhydroxybutyrate.

EXAMPLE 16
Comparative Homogeneous Hydrogenation of Methylacetoacetate Using (S)Ru-Binap Catalyst 0.0017 g of S-Ru-Binap is added to a mixture of 1.7 g of methylacetoacetate and 7.5 g of ethyleneglycol and allowed to react in the conditions as described in example 3. The conversion is less than 1% after 6 days.

EXAMPLE 17
Comparative Homogeneous Hydrogenation of Methylacetoacetate Using (S)Ru-Binap Catalyst 0.0017 g of S-Ru-Binap is added to a mixture of 1.7 g of methylacetoacetate and 7.5 g of methanol and allowed to react in the conditions as described in example 3. The conversion is less than 5% after 6 days.

EXAMPLE 18
Heterogeneous Asymmetric Hydrogenation of a Naphthylalanine Precursor According to the Invention A solution of 0.5 g ethyl-1-acetamido-2-(2-naphthyl)-acrylate (0.0018 mol) and 2.9 g (R)-Binap-Ru on Zeolite catalyst, prepared as described in example 13 (S/C of 75), in 25 ml degased methanol was vigorously stirred under hydrogen (100 psi) for 3 h at room temperature. Centrifugation of the slurry left a solution which was analyzed by Chiral HPLC to show 100% conversion and an enantiomeric excess (% ee) of 94.4%. Removal of solvent left a colourless residue that, after stirring in 10 ml of methyl tert.butylether gave a white solid of (L)-ethyl-1-acetamido-2-(2-naphthylalanine)ester.

EXAMPLE 19
Heterogeneous Asymmetric Hydrogenation of a Naphthylalanine Precursor According to the Invention with Successive Substrate Addition To a hydrogenation mixture, obtained as described in example 6, was added 0.5 g ethyl-1-acetamido-2-(2-naphthyl)-acrylate (0.0018 mol) and the slurry was vigorously stirred under nitrogen (100 psi) for 24 hours at room temperature. This process was repeated two times. Centrifugation of the slurry left a solution which was analyzed by Chiral HPLC to show 70% conversion and an enantiomeric excess (% ee) of 94.4% in (L) -ethyl-1-acetamido-2-(2-naphthylalanine)ester.

EXAMPLE 20
Preparation of the Catalyst According to the Invention (R-enantiomer) Using Zeolite BETA and Separate Dosage of Reagents 1 g of acid BETA zeolite—obtained from PQ corp. with a $SiO_2/Al_2O_3$ molar ratio of 21.6 and an average crystal size of 0.05 μm, determined by scanning electron microscopy— is impregnated with 0.0037 g of the R-enantiomer of the Binap ligand (2,2'-Bis(diphenylphosphino)-1,1'-binaphthyl), dissolved in 3 g of chloroform, for 3 hours under nitrogen flow. The powder obtained is then added to 0.0018 g of (p.cymene-ruthenium-chloride) dimer, dissolved in 20 ml of methanol, and stirred for 24 hours at 60° C. under reflux. Finally the suspension is dried under vacuum.

EXAMPLE 21
Heterogeneous Asymmetric Hydrogenation of a Naphthylalanine Precursor According to the Invention A solution of 0.5 g ethyl-1-acetamido-2-(2-naphthyl)-acrylate (0.0018 mol) and 0.5 g (R)-Binap-Ru on Zeolite catalyst, prepared as described in example 20 (S/C of 579), in 25 ml degased methanol was vigorously stirred under hydrogen (100 psi) for 72 h at room temperature. After removal of the catalyst and the solvent a colourless residue was obtained that, after stirring in 10 ml of methyl tert.butylether gave a white solid of (D)-ethyl-1-acetamido-2-(2-naphthylalanine)ester (yield 82% and 80.4% ee).

EXAMPLE 22
Preparation of the Catalyst According to the Invention (R-enantiomer) Using Zeolite BETA and Inverted Separate Dosage of Reagents 1 g of acid BETA zeolite—obtained from PQ corp. with a $SiO_2/Al_2O_3$ molar ratio of 21.6 and an average crystal size of 0.05 μm, determined by scanning electron microscopy— is impregnated with 0.0018 g of (p.cymene-ruthenium-chloride) dimer, dissolved in 3 g of chloroform, for 3 hours under nitrogen flow. The powder obtained is then added to 0.0037 g of the R-enantiomer of the Binap ligand (2,2'-Bis (diphenylphosphino)-1,1'-binaphthyl), and stirred for 24 hours in 20 ml of hexane at 60° C. under reflux. Finally the suspension is dried under vacuum.

EXAMPLE 23
Heterogeneous Asymmetric Hydrogenation of a Naphthylalanine Precursor According to the Invention A solution of 0.5 g ethyl-1-acetamido-2-(2-naphthyl)-acrylate (0.0018 mol) and 2.0 g (R)-Binap-Ru on Zeolite catalyst, prepared as described in example 22 (S/C of 145), in 25 ml degased methanol was vigorously stirred under hydrogen (100 psi) for 72 h at room temperature. Centrifugation of the slurry left a solution in methanol which was analyzed by Chiral HPLC to show 100% conversion and an enantiomeric excess (% ee) of 89.1%. Removal of the solvent left a colourless residue that, after stirring in 10 ml of methyl tert.butylether gave a white solid of (D)-ethyl-1-acetamido-2-(2-naphthylalanine)ester.

EXAMPLE 24
Preparation of the Catalyst According to the Invention (R-enantiomer) Using Zeolite BETA and Combined Dosage of Reagents 1 g of acid BETA zeolite—obtained from PQ corp. with a $SiO_2/Al_2O_3$ molar ratio of 21.6 and an average crystal size of 0.05 μm, determined by scanning electron microscopy— is impregnated with 0.0018 g of (p.cymene-ruthenium-chloride) dimer and 0.0037 g of the R-enantiomer of the Binap ligand (2,2'-Bis (diphenylphosphino)-1,1'-binaphthyl), dissolved in 3 ml of ethanol and 1 ml of dichloromethane, for 3 hours under nitrogen flow. A dry yellowish powder is obtained.

EXAMPLE 25
Heterogeneous Asymmetric Hydrogenation of a Naphthylalanine Precursor According to the Invention A solution of 0.5 g ethyl-1-acetamido-2-(2-naphthyl)-acrylate (0.0018 mol) and 2.0 g (R)-Binap-Ru on Zeolite catalyst, prepared as described in example 24 (S/C of 145), in 25 ml degased methanol was vigorously stirred under hydrogen (100 psi) for 48 h at room temperature. Centrifugation of the slurry left a solution in methanol which was analyzed by chiral HPLC to show 100% conversion and an enantiomeric excess (% ee) of 78.6%. Removal of the solvent left a colourless residue that, after stirring in 10 ml of methyl tert.butylether gave a white solid of (D)-ethyl-1-acetamido-2-(2-naphthylalanine)ester.

EXAMPLE 26
Preparation of the Catalyst According to the Invention (R-enantiomer) Using Zeolite NH4-BETA and (R)Ru-Binap)

1 g of acid BETA zeolite—obtained from PQ corp. with a $SiO_2/Al_2O_3$ molar ratio of 21.6 and an average crystal size of 0.05 µm, determined by scanning electron microscopy—is contacted with 0.5 l of an ammonia solution of pH 9.5 for 1 hour and then dried at 60° C. The obtained NH4-BETA zeolite is then used instead of H-BETA in the catalyst preparation according to example 1.

EXAMPLE 27
Comparative Hydrogenation of Methylacetoacetate

The catalyst used is prepared according to the example 26. The reaction mixture and conditions are the same as described in example 3. After 6 days the methylacetoacetate remains unconverted.

EXAMPLE 28
Heterogeneous Asymmetric Hydrogenation of a Naphthylalanine Precursor According to the Invention A solution of 0.5 g ethyl-1-acetamido-2-(2-naphthyl)-acrylate (0.0018 mol) and 2.0 g (R)-Binap-Ru on Zeolite catalyst, prepared as described in example 26 (S/C of 145), in 25 ml degased methanol was vigorously stirred under hydrogen (100 psi) for 48 h at room temperature. Centrifugation of the slurry left a solution in methanol which was analyzed by Chiral HPLC to show 100% conversion and an enantiomeric excess (% ee) of 79.9%. Removal of the solvent left a colourless residue that, after stirring in 10 ml of methyl tert.butylether gave a white solid of (D)-ethyl-1-acetamido-2-(2-naphthylalanine)ester.

EXAMPLE 29
Comparative Catalyst Preparation Using Zeolite ZSM-22

The catalyst is prepared according to example 1 but instead of H-BETA, ZSM-22—synthesized according to method A, described in EP-102,716 (1984), with a $SiO_2/Al_2O_3$ molar ratio of 92 and an average crystal size of 4 to 0.5 µm—is used as solid carrier.

EXAMPLE 30
Comparative Hydrogenation of Methylacetoacetate

The catalyst used is prepared according to the example 29. The reaction mixture and conditions are the same as described in example 3. After 6 days, no conversion is observed.

EXAMPLE 31
Comparative Catalyst Preparation Using Zeolite US-Y

The catalyst is prepared according to example 1 but instead of H-BETA, US Y obtained from PQ corp. with a $SiO_2/Al_2O_3$ molar ratio of 30 and an average crystal size of 0.5 µm is used as solid carrier.

EXAMPLE 32
Comparative Hydrogenation of Methylacetoacetate

The catalyst used is prepared according to the example 31. The reaction mixture and conditions are the same as described in example 3. After 6 days the conversion of methylacetoacetate is less than 3%.

EXAMPLE 33
Comparative Catalyst Preparation with the Ru-Precursor and Zeolite BETA 1 g of acid BETA zeolite—obtained from PQ corp. with a $SiO_2/Al_2O_3$ molar ratio of 21.6 and an average crystal size of 0.05 µm, determined by scanning electron microscopy is impregnated with 0.0018 g of (p-cymene-ruthenium chloride) dimer, dissolved in 1.7 g of methanol for 3 hours under nitrogen flow. A dry brownish powder is obtained.

EXAMPLE 34
Comparative Heterogeneous Asymmetric Hydrogenation of a Naphthylalanine Precursor The catalyst used is prepared according to the example 33. The reaction mixture and conditions are the same as described in example 5. After 2 days the conversion of the naphthylalanine precursor is 0%.

IR Characterization

IR characterization was performed on five different samples (KBr platelets):
- pure R-(+)-binap-p-cymene-ruthenium chloride
- the catalyst, prepared according to example 2
- a mechanical mixture of 0.1 g of R-(+)-binap-p-cymene-ruthenium chloride and 0.5 g of H-beta
- the catalyst, prepared according to example 20
- the catalyst, prepared according to example 22

Attention was focused on the adsorption band between 1440 and 1430 cm$^{-1}$. This band can be assigned to the interaction of phosphorous with aromatic groups, linked to it, resulting in activated ring vibrations of the aromatic groups (L. J. Bellamy, The Infra-Red Spectra of Complex Molecules, Chapman and Hall, London, p. 358/59 [1975]). Results are listed in Table I below.

TABLE I

| sample | band position |
|---|---|
| pure R-(+)-binap-p-cymene-ruthenium chloride | 1434.5 ± 0.5 cm$^{-1}$ |
| mechanical mixture of 0.01 g of R-(+)-binap-p-cymene-ruthenium chloride and 0.5 g of H-beta | 1434.5 ± 0.5 cm$^{-1}$ |
| catalyst, prepared according to example 2 | 1436.7 ± 0.5 cm$^{-1}$ |
| catalyst, prepared according to example 20 | 1436.2 ± 0.5 cm$^{-1}$ |
| catalyst, prepared according to example 22 | 1436.7 ± 0.5 cm$^{-1}$ |

The catalysts prepared according to the invention show a significant shift in the vibration from 1434.5±0.5 cm$^{-1}$ in the original complex to a higher wave number.

We claim:

1. A chiral solid catalyst, comprising a zeolite and a metal-binap complex, wherein the zeolite is a BEA topology zeolite.

2. The catalyst as claimed in claim 1, wherein the catalyst particles are of the size 0.005–1.0 µm.

3. The catalyst as claimed in claim 1, wherein the BEA topology zeolite is a BETA zeolite.

4. The catalyst as claimed in claim 1, wherein the zeolite is an acid BEA topology zeolite.

5. The catalyst as claimed in claim 4, wherein the acid BEA topology zeolite is an acid NU-2 zeolite.

6. The catalyst as claimed in claim 1, wherein the zeolite aluminum is partially or completely substituted by a metal ion.

7. The catalyst as claimed in claim 1, wherein the zeolite is an ammonium BEA topology zeolite.

8. The catalyst as claimed in claim 1, wherein one of the ligands of the metal-binap complex is R- or S-binap.

9. The catalyst as claimed in claim 1, wherein the metal-binap complex comprises a metal selected from the group consisting of Ru, Ir, P, Ni, and Rh.

10. The catalyst as claimed in claim 1, wherein the catalyst comprises less than 10 wt % metal-binap complex.

11. A process for the preparation of a catalyst according to claim 1, wherein the zeolite is impregnated with a binap complex.

12. A process for the preparation of a catalyst according to claim 11, wherein the BEA topology zeolite is impregnated simultaneously or successively with the constituents of the binap complex.

13. A process according to claim 12, wherein the BEA topology zeolite is first impregnated with the binap ligand and thereafter with the metal, thereby forming the complex in situ on the zeolite.

14. A process according to claim 12, wherein the BEA topology zeolite is first impregnated with the metal and thereafter with the binap ligand, thereby forming the complex in situ on the zeolite.

15. The catalyst as claimed in claim 1, wherein the catalyst particles are of the size 0.01–0.5 $\mu$m.

16. The catalyst as claimed in claim 1, wherein the catalyst particles are of the size 0.02–0.1 $\mu$m.

17. The catalyst as claimed in claim 1, wherein the catalyst comprises 0.05–5 wt % metal-binap complex.

18. The catalyst as claimed in claim 1, wherein the catalyst comprises 0.2–1 wt % metal-binap complex.

19. A method for the production of substantially enantiomerically pure products from prochiral starting material, wherein the catalyst according to claim 1 catalyzes the production of said substantially enantiomerically pure products.

20. The method as claimed in claim 19, wherein the starting material to catalyst ratio is 0.1–1000, wt/wt.

21. The method as claimed in claim 19, wherein the method is carried out in a solvent having a dielectric constant $\epsilon$ between 30 and 80.

22. The method as claimed in claim 19, wherein the starting materials are prochiral unsaturated substrates.

23. The method as claimed in claim 22, wherein the starting materials are chosen from the group consisting of beta functionalized ketones, betaketoesters, functionalized olefins, and $\alpha$-$\beta$ unsaturated functionalized olefins.

24. The method as claimed in claim 19, wherein the method comprises heterogeneous asymmetric hydrogenation.

25. The method as claimed in claim 19, wherein the starting material to catalyst ratio is 2–100 wt/wt.

* * * * *